(12) United States Patent
Gambhir et al.

(10) Patent No.: US 10,869,940 B2
(45) Date of Patent: Dec. 22, 2020

(54) TARGETED PHOTOACOUSTIC COMPOUNDS, FORMULATIONS, AND USES THEREOF

(71) Applicant: The Board of Trustees of the Leland Stanford Junior University, Palo Alto, CA (US)

(72) Inventors: Sanjiv S. Gambhir, Portola Valley, CA (US); Jelena Levi, Palo Alto, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 926 days.

(21) Appl. No.: 15/180,418

(22) Filed: Jun. 13, 2016

(65) Prior Publication Data
US 2016/0361446 A1    Dec. 15, 2016

Related U.S. Application Data

(60) Provisional application No. 62/174,833, filed on Jun. 12, 2015.

(51) Int. Cl.
*A61B 8/00* (2006.01)
*A61K 49/22* (2006.01)
*A61K 49/00* (2006.01)

(52) U.S. Cl.
CPC ........ *A61K 49/221* (2013.01); *A61K 49/0017* (2013.01)

(58) Field of Classification Search
None
See application file for complete search history.

(56) References Cited

U.S. PATENT DOCUMENTS

| | | | |
|---|---|---|---|
| 4,446,122 A | 5/1984 | Chu et al. | |
| 4,862,851 A | 9/1989 | Washino et al. | |
| 4,902,615 A | 2/1990 | Freeman et al. | |
| RE33,405 E | 10/1990 | Chu et al. | |
| 4,970,299 A | 11/1990 | Bazinet et al. | |
| 5,055,404 A | 10/1991 | Ueda et al. | |
| 5,162,504 A | 11/1992 | Horoszewicz | |
| 5,786,204 A | 7/1998 | He et al. | |
| 7,163,680 B2 | 1/2007 | Bander | |
| 7,592,435 B2* | 9/2009 | Milton ............... | C12Q 1/686 536/23.1 |
| 8,178,360 B2* | 5/2012 | Barnes ............... | A61K 49/0041 435/6.1 |
| 8,227,634 B2 | 7/2012 | Pomper et al. | |
| 8,778,305 B2 | 7/2014 | Pomper et al. | |
| 8,926,944 B2 | 1/2015 | Babich et al. | |
| 2001/0012890 A1 | 8/2001 | Thompson | |
| 2002/0150578 A1 | 10/2002 | He et al. | |
| 2003/0003103 A1 | 1/2003 | Thompson | |
| 2004/0156846 A1 | 8/2004 | Daum et al. | |
| 2005/0019870 A1 | 1/2005 | Afar et al. | |
| 2006/0269557 A1 | 11/2006 | Sherman et al. | |
| 2009/0087860 A1* | 4/2009 | Todd ................... | C07K 16/3069 435/7.1 |
| 2015/0110715 A1* | 4/2015 | Eder .................. | A61K 51/0402 424/1.65 |
| 2015/0125904 A1* | 5/2015 | Ting ..................... | G01N 33/532 435/68.1 |

OTHER PUBLICATIONS

Chen et al. (Bioconj. Chem. 2012, 23, 2377-2385).*
Boutet et al. (J. Biomed. Optics 2009, 14, 064001-1 to 064001-7).*
Swift et al. (Proc. SPIE 2001, 4252, 47-58).*
Kupstat et al. (Bioconj. Chem. 2011, 22, 2546-2557).*
Rudat et al. (Eur. J. Med. Chem. 2011, 46, 4457-4465).*
Kantoff, Introduction, Clinical Presentation and Diagnosis of Prostate Cancer. Available online: http://www.uptodate.com/contents/clinical-presentation-and-diagnosis-of-prostate-cancer. Accessed May 31, 2013. pp. 1-2.
Kelloff et al., 2009. Challenges in clinical prostate cancer: role of imaging. AJR Am J Roentgenol. 192: 1455-1470.
Hricak et al., 2007. Imaging prostate cancer: a multidisciplinary perspective. Radiology. 243: 28-53.
Wang & Hu, 2012. Photoacoustic tomography: in vivo imaging from organelles to organs. Science. 335: 1458-1462.
Bauer et al., 2011. 3-D photoacoustic and pulse echo imaging of prostate tumor progression in the mouse window chamber. J Biomed Opt. 16(2): 1-10.
Wang et al., 2010. Photoacoustic tomography: a potential new tool for prostate cancer. Biomed Opt Express. 1: 1117-1126.
Olafsson et al., 2010. Real-time, contrast enhanced photoacoustic imaging of cancer in a mouse window chamber. Opt Express. 18: 18625-18632.
Kim et al., 2007. Indocyanine-green-embedded PEBBLEs as a contrast agent for photoacoustic imaging. J Biomed Opt. 12(4): 1-8.
Agarwal et al., 2007. Targeted gold nanorod contrast agent for prostate cancer detection by photoacoustic imaging. Journal of Applied Physics. 102: 1-4.
Kundavaram et al., 2012. Value of contrast-enhanced ultrasonography in prostate cancer. Current Opinion in Urology. 22: 303-309.
Turkbey et al., 2009. Imaging techniques for prostate cancer: implications for focal therapy. Nature Reviews Urology. 6: 191-203.
Gupta et al., 2013. The state of prostate MRI in 2013. Oncology (Williston Park). 27: 262-270.
Grauer et al., 1998. Identification, purification, and subcellular localization of prostate-specific membrane antigen PSM' protein in the LNCaP prostatic carcinoma cell line. Cancer Res. 58: 4787-4789.

(Continued)

Primary Examiner — Michael G. Hartley
Assistant Examiner — Melissa J Perreira
(74) Attorney, Agent, or Firm — Thomas | Horstemeyer, LLP

(57) ABSTRACT

Provided herein are targeted photoacoustic compounds and formulations thereof that can contain a photoacoustic signaling moiety operatively coupled to a targeting moiety. Also provided herein are methods of imagining a subject using the targeted photoacoustic compounds and formulations thereof provided herein.

9 Claims, 4 Drawing Sheets

(56) References Cited

OTHER PUBLICATIONS

Zhou et al., 2005. NAAG peptidase inhibitors and their potential for diagnosis and therapy. Nat Rev Drug Discov. 4: 1015-1026.
Liu et al., 1997. Monoclonal antibodies to the extracellular domain of prostate-specific membrane antigen also react with tumor vascular endothelium. Cancer Res. 57: 3629-3634.
Lapidus et al., 2000. Prostate-specific membrane antigen (PSMA) enzyme activity is elevated in prostate cancer cells. Prostate. 45: 350-354.
Silver et al., 1997. Prostate-specific membrane antigen expression in normal and malignant human tissues. Clin Cancer Res. 3: 81-85.
Afshar-Oromieh et al., 2012. [68Ga]Gallium-labelled PSMA ligand as superior PET tracer for the diagnosis of prostate cancer: comparison with 18F-FECH. Eur J Nucl Med Mol Imaging. 39: 1085-1086.
Cho et al., 2012. Biodistribution, tumor detection, and radiation dosimetry of 18F-DCFBC, a low-molecular-weight inhibitor of prostate-specific membrane antigen, in patients with metastatic prostate cancer. J Nucl Med. 53: 1883-1891.
Mease et al., 2013. PET imaging in prostate cancer: focus on prostate-specific membrane antigen. Curr Top Med Chem. 13: 951-962.
Minner et al., 2011. High level PSMA expression is associated with early PSA recurrence in surgically treated prostate cancer. Prostate. 71: 281-288.
Beheshti et al., 2014. BAY 1075553 PET-CT for Staging and Restaging Prostate Cancer Patients: Comparison with [F] Fluorocholine PET-CT (Phase I Study). Mol Imaging Biol. pp. 424-433.
Afshar-Oromieh et al., 2013. PET imaging with a [68Ga] gallium-labelled PSMA ligand for the diagnosis of prostate cancer: biodistribution in humans and first evaluation of tumour lesions. Eur J Nucl Med Mol Imaging. 40: 486-495.
Maund et al., 2014. Optimization and comprehensive characterization of a faithful tissue culture model of the benign and malignant human prostate. Lab Invest. 94: 208-221.
Elsasser-Beile et al., 2006. Prostate, 66:1359-1370.
Liu et al., 1998. Cancer Res., 58:4055-4060.
Fracasso et al., 2002. Prostate, 53:9-23.
McDevitt et al., 2000. Cancer Res., 60:6095-6100.
McDevitt et al., 2001. Science, 294: 1537-1540.
Smith-Jones et al., 2000. Cancer Res., 60:5237-5243.
Vallabhajosula et al., 2004. Prostate, 58: 145-155.
Bander et al., 2003. J. Urol., 170: S84-S89.
Patri et al., 2004. Bioconj. Chem., 15:1174-1181.
Horoszewicz et al., 1987. Anticancer Res., 7:927-936.
Chang et al., 1999. Cancer Res., 59:3192-3198.
Murphy et al., 1998, J. Urol., 160:2396-2401.
Grauer et al., 1998. Cancer Res., 58:4787-4789.
Wang et al., 2001. Int. J. Cancer, 92:871-876.
Vihko et al., 1985. Biotechnology in Diagnostics, 131.
Babaian et al., 1987. J. Urol., 137:439-443.
Leroy et al., 1989. Cancer, 64:1-5.
Meyers et al., 1989. Prostate, 14:209-220.
Levi et al., 2014. A High-Affinity, High-Stability Photoacoustic Agent for Imaging Gastrin—Releasing Peptide Receptor in Prostate Cancer Clinical Cancer Research. 3721-3729.
Fenner, Nature Reviews Urology 11, 424, 2014. Research Highlights. In Brief. Published online Jul. 15, 2014. 1.

* cited by examiner

Formula 1

TARGETED PHOTOACOUSTIC COMPOUNDS, FORMULATIONS, AND USES THEREOF

CROSS-REFERENCE TO RELATED APPLICATIONS

This application claims the benefit of and priority to U.S. Provisional Patent Application No. 62/174,833, filed on Jun. 12, 2015, entitled "TARGETED PHOTOACOUSTIC COMPOUNDS, FORMULATIONS, AND USES THEREOF," the contents of which is incorporated by reference herein in its entirety.

BACKGROUND

Cancer refers to a group of diseases involving abnormal cell growth with the potential to invade or spread to other parts of the body. It is estimated that there are over 100 different known cancers that affect humans. Approximately 14.1 million new cases of cancer were diagnosed in 2012 and cancer accounted for about 8.2 million deaths or 14.6% of all deaths world-wide. Cancer costs the United States about $1.16 trillion dollars per year. Given the prevalence and cost of cancer world-wide there is an ongoing need for improved diagnostics, preventives and therapeutics.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
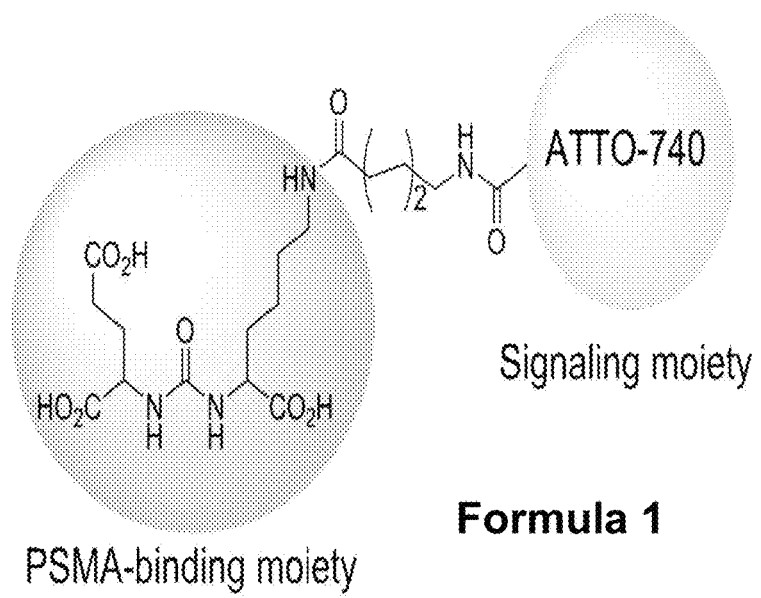
FIG. 1 shows one embodiment of a targeted photoacoustic compound as described herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

Unless otherwise defined herein, the following terms as used herein are defined as follows:

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

As used herein, "about," "approximately," and the like, when used in connection with a numerical variable, generally refers to the value of the variable and to all values of the variable that are within the experimental error (e.g., within the 95% confidence interval for the mean) or within +−10% of the indicated value, whichever is greater.

As used herein, "control" is an alternative subject or sample used in an experiment for comparison purposes and included to minimize or distinguish the effect of variables other than an independent variable. A "control" can be positive or negative.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to a an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "purified" is used in reference to a nucleic acid sequence, peptide, or polypeptide or other compound that has increased purity relative to the natural environment or the environment in which it was produced in.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "therapeutic" refers to treating or curing a disease or condition.

As used herein, "preventative" refers to hindering or stopping a disease or condition before it occurs or while the disease or condition is still in the sub-clinical phase.

As used herein, "separated" refers to the state of being physically divided from the original source or population such that the separated compound, agent, particle, chemical compound, or molecule can no longer be considered part of the original source or population.

As used herein, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data in stored on a suitable device such as a flash memory or CD-ROM.

As used herein, "chemotherapeutic agent" or "chemotherapeutic" refer to a therapeutic agent utilized to prevent or treat cancer.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, "antibody" refers to a protein produced by B cells that is used by the immune system to identify and neutralize foreign compounds, which are also known as antigens. Antibodies are glycoproteins belonging to the immunoglobulin superfamily. Antibodies, recognize and bind to specific epitopes on an antigen.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "specific binding partner" or "binding partner" is a compound or molecule to which a second compound or molecule binds with a higher affinity than all other molecules or compounds.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein "immunomodulator," refers to an agent, such as a therapeutic agent, which is capable of modulating or regulating one or more immune function or response.

As used herein, "targeting moiety" refers to a moiety or molecule that localizes to or away from a specific local, cell, and/or other molecule.

As used herein, "differentially expressed," refers to the differential production of RNA, including, but not limited to, mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "variant" refers to a polypeptide that differs from a reference polypeptide or compound, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. A typical variant of a compound can be a derivative or analogue thereof.

As used herein, "functional variant" refers to a variant of a protein, polypeptide, molecule or compound (e.g., a variant of folic acid or a folic acid receptor protein) that can perform the same functions or activities as the original protein or polypeptide, although not necessarily at the same level (e.g., the variant may have enhanced, reduced or changed functionality, so long as it retains the basic function).

As used herein, "anti-infective" refers to compounds or molecules that can either kill an infectious agent or inhibit it from spreading. Anti-infectives include, but are not limited to, antibiotics, antibacterials, antifungals, antivirals, and antiprotazoans.

As used herein, "wild-type" is the typical form of an organism, variety, strain, gene, protein, or characteristic as it occurs in nature, as distinguished from mutant forms that may result from selective breeding or transformation with a transgene.

As used herein "induces," "inducing," or "induced" refers to activating or stimulating a process or pathway within a cell.

As used herein "heterogeneous" refers to a population of molecules, including nanoparticles, proteins, and polypeptides, or a population of subunits of a molecule that contains at least 2 molecules or subunits that are different from one another.

As used herein "homogenous" refers to a population of molecules, including nanoparticles, proteins, and polypeptides, or a population of subunits of a molecule in which all the molecules or subunits are identical to one another.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "composition" refers to a combination of an active agent(s) and another compound or composition, inert (for example, a detectable agent or label) or active, such as an adjuvant.

As used herein, "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, C1-C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl) C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl) amino, carbamoyl, (C1-C6 alkyl)carbonyl, (C1-C6 alkoxy) carbonyl, (C1-C6 alkyl)aminocarbonyl, di-(C1-C6 alkyl) aminocarbonyl, arylcarbonyl, aryloxycarbonyl, (C1-C6 alkyl)sulfonyl, and arylsulfonyl. The groups listed above as suitable substituents are as defined hereinafter except that a suitable substituent may not be further optionally substituted.

As used herein, "optically substituted" indicates that a group may be unsubstituted or substituted with one or more substituents as defined herein.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, and $C_3$-$C_{30}$ for branched chains). In other embodiments, a straight chain or branched chain alkyl contains 20 or fewer, 15 or fewer, or 10 or fewer carbon atoms in its backbone. Likewise, in some embodiments cycloalkyls have 3-10 carbon atoms in their ring structure. In some of these embodiments, the cycloalkyl have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

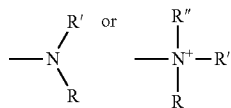

wherein R, R', and R" each independently represent a hydrogen, an alkyl, an alkenyl, —(CH2)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

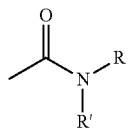

wherein R and R' are as defined above.

As used herein, "Aryl" refers to C$_5$-C$_{10}$-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H, 6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

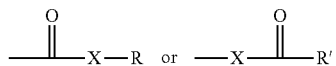

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium.

As used herein, the term "nitro" refers to —NO$_2$; the term "halogen" designates —F, —Cl, —Br, or —I; the term "sulfhydryl" refers to —SH; the term "hydroxyl" refers to —OH; and the term "sulfonyl" refers to —SO$_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, peptide, and polypeptide groups.

Heteroatoms, such as nitrogen, may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "effective amount" refers to the amount of a targeted photoacoustic compound or derivative thereof or auxiliary agent described herein that will elicit the diagnostic, biological or medical response of a tissue, system, animal, or human that is being sought by the researcher, veterinarian, medical doctor or other clinician. "Effective amount" includes that amount of targeted photoacoustic compound or derivative thereof or auxiliary agent described herein described herein that, when administered, is sufficient to emit ultrasonic waves after light stimulation at the appropriate wavelength for the photoacoustic signaling molecule, render the targeted photoacoustic compound capable of acting as an ultrasound contrast agent, prevent development of, alleviate to some extent, one or more of the symptoms of a cancer or other abnormality being treated or diagnosed. The effective amount will vary depending on the exact chemical structure of the targeted photoacoustic compound or derivative thereof or auxiliary agent, the location of the tumor, the tissue type being imaged, the severity and/or type of the cancer or other disease, disorder, syndrome, or symptom thereof being treated, the route of administration, the time of administration, the rate of excretion, the drug combination, the judgment of the treating physician, the dosage form, and the age, weight, general health, sex and/or diet of the subject to be treated.

As used herein, "structural analogue" refers to a compound, molecule, protein, and the like, that has a structure similar to that of another compound, but is different in one aspect, such as an atom, functional group.

As used herein, "functional analogue" refers to a compound molecule, protein, and the like, that has the same or similar physical, chemical, biochemical, pharmacological properties, or elicit the same effect as another molecule, protein, and the like. In some embodiments, functional analogues are also structural analogues. In other embodiments, functional analogues are not structural analogues.

As used herein, "analogue" refers to of both the terms "structural analogue" and "functional analogue."

As used herein, "operatively linked," "operatively link," and the like refer to an association of two or more molecules or compounds that is not a covalent bond. Types of associations between two or more molecules or compounds that are "operatively linked" includes ionic associations, electrostatic interactions, hydrostatic interactions, van der Waals interactions, and the like. "Operatively linked" also includes any reversible bonds or associations between two or more molecules or compounds such that a compound or molecule is releasable. This type of interaction is also referred to herein as "releasable" or a "releasable link." Operatively linked," "operatively link" and the like also include the association of encapsulation between two or more molecules.

As used herein, "encapsulation," "encapsulate," "encapsulated" and the like refer to the confinement, containment, or association of one individual molecule or compound within another individual molecule or compound. In some embodiments, "encapsulation," "encapsulate," "encapsulated" and the like refer to the confinement, containment, or association of a targeted photoacoustic compound as part of a nanoparticle or liposomal formulation.

As used herein, "conjugate" or "conjugated" refer to a covalent bond or a bond of similar strength and permanence of a covalent bond. "Conjugate" also includes irreversible bonds between two or more molecules or compounds.

As used herein, "coupled" or "coupled to" refers to the attachment of one molecule to another via one or more additional molecules. "Coupled" includes both "conjugate" and "operatively linked."

As used herein, "single-chain Fvs" refer to recombinant antibody fragments contain only the variable light chain (VL) and variable heavy chain (VH) covalently connected to one another by a polypeptide linker. Either the VL or HL can be at the N-terminal domain. The polypeptide linker can be of variable length and composition, so long as the two variable domains are bridged without significant steric interference. Linkers can include stretches of glycine and serine residues with some glutamate or lysine residues interspersed. scFvs can be monomeric or dimeric (and form a diabody).

As used herein, "diabodies" are dimeric scFvs and can have shorter linkers than monomeric scFvs.

As used herein, "Fv fragment" refers to an antibody fragment that contains one VH and one VL domain connected to one another via noncovalent interactions.

As used herein, "dsFv" refers to an Fv with an engineered intermolecular disulfide bond.

As used herein, "Fab fragment" refers to as an antibody fragment essentially equivalent to that obtained by digestion of immunoglobulins with an enzyme (e.g. papin). The Fab fragment can be enzymatically or recombinantly produced. The heavy chain segment of the Fab fragment is referred to as the Fd fragment.

Discussion

Prostate cancer is the most common cancer type in American men. The American Cancer Society estimates that in 2015 there will be about 221,000 new cases of prostate cancer and about 27,540 deaths due to prostate cancer. This makes prostate cancer the second leading cause of death in American men, behind only lung cancer. About 1 in 7 men will be diagnosed with prostate cancer during their lives and 1 in 38 will die from it. Prostate cancers include adenocarcinomas, sarcomas, small cell carcinomas, neuroendocrine tumors, and transitional cell carcinomas. In most cases, the prostate cancer is an adenocarcinoma.

Current clinical diagnosis of prostate cancer is made upon histological examination of biopsy tissue, which is indicated for patients with abnormal levels of prostate specific antigen (PSA) or abnormal rectal examination results. The biopsy is not lesion directed as current transrectal ultrasound (TRUS) imaging techniques used to guide the procedure lack the specificity to identify malignancies and is used only to provide anatomical references within the prostate. Although imaging plays an important role in all aspects of prostate cancer patient management from diagnosis to treatment, no imaging modality serves as a diagnostic tool for prostate cancer.

With the aforementioned deficiencies in mind, described herein are compounds and formulations thereof that can serve as imaging agents capable of facilitating primary diagnosis of prostate cancer as well as can provide a means for lesion-directed image guided biopsy. They can include a targeted photoacoustic imaging agent that contains a targeting moiety coupled to a photoacoustic signaling molecule via a linker. In some embodiments, the targeting moiety can bind prostate-specific membrane antigen (PSMA). The targeted photoacoustic agents described herein can be used as imaging agents during optical and photoacoustic imaging procedures. The imaging methods described herein can be capable of imaging both vasculature and molecular profile outside the blood vessels of prostate tumors.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Targeted Photoacoustic Compounds and Formulations Thereof

Targeted Photoacoustic Compounds

Photoacoustic imaging (PAI) is a hybrid imaging modality closely related to ultrasound and is based on the photoacoustic effect. In PAI, non-ionizing laser pulses can be delivered into biological tissues. Some of the delivered energy can be absorbed and converted into heat and lead to transient thermoplastic expansion and thus wideband (i.e., MHz) ultrasonic emission. The ultrasonic waves generated can be detected by ultrasonic transducers and analyzed and converted into images. The targeted photoacoustic compounds described herein can include a targeting moiety coupled to a photoacoustic signaling molecule via a linker. The targeted photoacoustic compounds can target specific molecules, cells, or tissues (targets) and deliver a photoacoustic signaling molecule to the target and thus can allow for photoacoustic imaging of specific targets.

Targeting Moieties

The targeted photoacoustic compounds include a targeting moiety. The targeting moiety can specifically bind a molecule or component associated with an organ, tissue, cell, cell membrane, extracellular matrix, and/or intracellular compartment. These molecules or components are also referred to herein as "targets" or "markers". The targeting moieties can bind to a target that is associated with a specific developmental stage, physiologic state, disease, disorder, disease state, and/or disorder state. In some embodiments, the target is expressed in a cancerous or pre-cancerous cell.

The targeting moieties described herein can specifically bind to or otherwise specifically interact with a prostate-specific membrane antigen (PSMA). The PSMA can be on a prostate cancer cell. Suitable PSMA targeting moieties include, but are not limited to N-acetylaspartylglutamate and analogues or derivatives thereof, aptamers, antibodies, thiol based PSMA substrates, hydroxamate based PSMA substrates and derivatives thereof, conformationally constricted dipeptide mimetics, PBDA-based and urea-based PSMA substrates. PBDA-based can refer to compounds that are derivatives of PBDA or otherwise include PBDA.

N-Acetylaspartylglutamate, Analogues Thereof, and Derivatives Thereof

The targeting moiety can be N-acetylaspartylglutamate (NAAG) (Formula 2), an analogue thereof, or a derivative thereof. NAAG is a substrate of PSMA (also known as Glutamate carboxypeptidase II). Methods of making NAAG, derivatives thereof, and analogues will be appreciated by those skilled in the art.

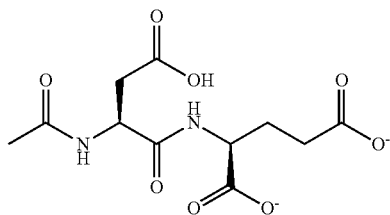

Formula 2

The targeting moiety can be 2-PMPA (Formula 3) (2-(phosphonomethyl)pentane-1,5 dioic acid, analogues thereof, or derivatives thereof. 2-PMPA is a phosphonate analogue of NAAG that contains a glutamate analog moiety conjugated to phosphonic acid. Another suitable derivative of 2-PMPA can be a compound according to Formula 4. Methods of making 2-PMPA, derivatives thereof, and analogues will be appreciated by those skilled in the art.

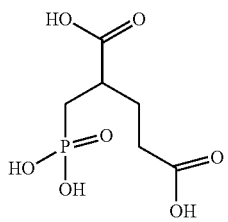

Formula 3

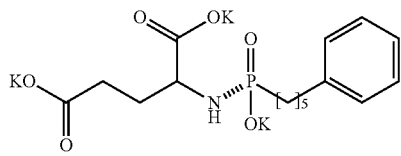

Formula 4

Aptamers

Generally, the targeting function of an aptamer is based on the three-dimensional structure of the aptamer. The binding of an aptamer to a target can be mediated by the interaction between the two- and/or three-dimensional structures of both the aptamer and the target. In some embodiments, the aptamers can bind PSMA. Methods of making and determining PSMA binding aptamers are generally known in the art. The PSMA targeting aptamer can be the A10 aptamer (SEQ ID NO: 1 GGGAGGACGAUGCGGAUCAGCCAU-GUUUACGUCACUCCUUGUCAAU CCUCAUCGGCA-GACGACUCGCCCGA), the A9 aptamer (SEQ ID NO: 2 GGGAGGACGAUGCGGACCGAAAAAGACCUGAC-UUCUAUACUAAGUC UACGUUCCCAGACGA-CUCGCCCGA), derivatives thereof, and/or characteristic portions thereof. The nucleic acids forming the aptamers can contain modified nucleosides, nucleosides with hydrocarbon linkers (e.g., an alkylene) or polyether linkers (e.g. PEG). Suitable modifications can be those where they do not reduce the dissociation constant of the aptamer for the target greater than about $1\times10^{-3}$ M.

Antibodies

Antibodies can bind specifically to epitopes on targets. The antibodies can be monoclonal (mAb) or polyclonal. Methods of designing, producing, and testing antibodies are generally known in the art. In some embodiments, the targeting moiety can be an antibody that specifically binds to PSMA. Such antibodies include, but are not limited to, scFv (single-chain Fvs) antibodies AS, GO, G1, G2, and G4 and mAbs 3/E7, 3/F11, 3/A12, K7, K12, and D20 (Elsasser-Beile et al., 2006, Prostate, 66:1359); mAbs E99, J591, J533, and J415 (Liu et al., 1997, Cancer Res., 57:3629; Liu et al., 1998, Cancer Res., 58:4055; Fracasso et al., 2002, Prostate, 53:9; McDevitt et al., 2000, Cancer Res., 60:6095; McDevitt et al., 2001, Science, 294: 1537; Smith-Jones et al., 2000, Cancer Res., 60:5237; Vallabhajosula et. al., 2004, Prostate, 58: 145; Bander et al., 2003, J. Urol., 170: 1717; Patri et al., 2004, Bioconj. Chem., 15:1174; and U.S. Pat. No. 7,163,680); mAb 7E11-05.3 (Horoszewicz et al., 1987, Anticancer Res., 7:927); antibody 7E11 (Horoszewicz et al., 1987, Anticancer Res., 7:927; and U.S. Pat. No. 5,162,504); and antibodies described in Chang et al., 1999, Cancer Res., 59:3192; Murphy et al., 1998, J. Urol., 160:2396; Grauer et al., 1998, Cancer Res., 58:4787; and Wang et al., 2001, Int. J. Cancer, 92:871.

In some embodiments, antibodies which recognize other prostate tumor-associated antigens are known in the art and can be used in accordance with the present invention to target cells associated with prostate cancer tumors (see, e.g., Vihko et al., 1985, Biotechnology in Diagnostics, 131; Babaian et al., 1987, J. Urol., 137:439; Leroy et al., 1989, Cancer, 64:1; Meyers eta!., 1989, Prostate, 14:209; and U.S. Pat. Nos. 4,970,299; 4,902,615; 4,446,122 and Re 33,405; 4,862,851; 5,055,404). To give but a few examples, antibodies have been identified, which recognize transmembrane protein 24P4C12 (U.S. Patent Publication 2005/0019870); calveolin (U.S. Patent Publications 2003/0003103 and 200110012890); L6 (U.S. Patent Publication 2004/0156846); prostate specific reductase polypeptide (U.S. Pat. No. 5,786,204; and U.S. Patent Publication 2002/0150578); and prostate stem cell antigen (U.S. Patent Publication 2006/0269557).

Thiol-Based PSMA Substrates

The targeting moiety can be a thiol based PSMA substrate. The thiol based substrate can be 2-MPPA (2-(3-mercaptopropyl)pentanedioic acid, Formula 5) or suitable derivatives or analogues thereof. Methods of making thiol-based PSMA substrates and derivatives or analogues thereof will be appreciated by those skilled in the art.

Formula 5

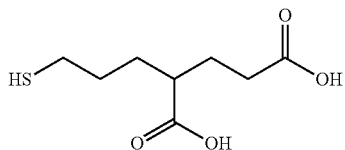

The thiol based substrate can be an indole thiol or suitable derivatives or analogues thereof. In some embodiments, the indole thiol can have a formula according to Formula 6, wherein R is H or —O-Me.

Formula 6

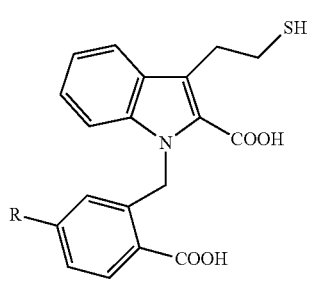

Hydroxamate Based PSMA Substrates

The targeting moiety can be hydroxamate based PSMA substrates. Hydroxamate based PSMA substrates can be based on 2-PMPA or 2-MPPA. In some embodiments, the hydroxamate based PSMA substrate can be according to Formula 7, wherein n can range from 1-50. Methods of making hydroxamate based PSMA substrates will be appreciated by those skilled in the art.

Formula 7

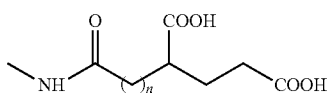

Conformationally Constricted Dipeptide Mimetics

The targeting moiety can be a conformationally constricted dipeptide mimetic. The conformationally constricted dipeptide mimetic can be a NAAG analogue containing a six-membered ring. The conformationally constricted dipeptide mimetic can be according to Formula 8, 9, or 10. Methods of making conformationally constricted dipeptide mimetics will be appreciated by those skilled in the art.

Formula 8

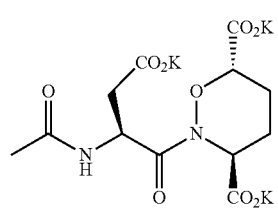

Formula 9

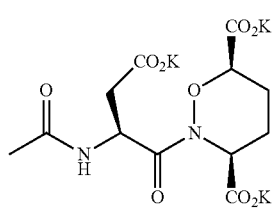

Formula 10

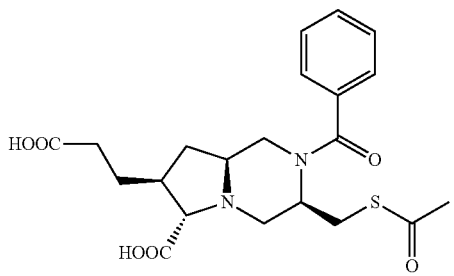

PBDA and Urea Based PSMA Substrates

The targeting moiety can be a PBDA or urea based PSMA substrate. Suitable PBDA based and urea-based substrates can have a formula according to Formula 11:

Formula 11

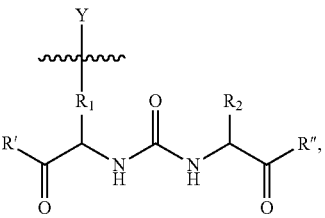

where $R_1$ can be optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

$R_2$ can be optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, or optionally substituted carbocyclic;

R' and R" can be each independently —$OR_4$, —$SR_4$, —$SOR_4$, —$SO_2R_4$, —$N(R_3)S(O)_2$—$R_4$, —$N(R_3)(SO_2)NR_3R_4$, —$NR_3R_4$, —$C(O)$—$O$—$R_4$, —$C(O)R_4$, —$C(O)NR_3R_4$, or —$N(R_3)C(O)R_4$; $R_3$ and $R_4$ can each be independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic.

In other embodiments, R' and R" can each be independently —$OR_4$.

In another embodiment, each $R_4$ can be independently H, methyl, or ethyl.

In certain embodiments, $R_1$ can be a side chain of a naturally occurring amino acid.

In other embodiments, $R_1$ can be optionally substituted alkyl, containing 0, 1, 2, or 3 heteroatoms selected from O, S, or N; optionally substituted arylalkyl, optionally substituted alkoxy, or optionally substituted heterocyclic.

In a further embodiment, $R_1$ can be $(CH_2)_p$—O—Y, $(CH_2)_p$—S—Y, $(CH_2)_p$—SO—Y, $(CH_2)_p$—SO_2—Y, $(CH_2)_p$—N(R_3)S(O)_2—Y, $(CH_2)_p$—N(R_3)(SO_2)NR_3—Y, $(CH_2)_p$—NR_3—Y, $(CH_2)_p$—C(O)—O—Y, $(CH_2)_p$—C(O)—Y, $(CH_2)_p$—C(O)NR_3—Y, or $(CH_2)_p$—N(R_3)C(O)—Y; $R_3$ and $R_4$ can each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 1-6. In still a further embodiment, $R_1$ can be $(CH_2)_p$—O—Y, $(CH_2)_p$—NR_3—Y, $(CH_2)_p$—C(O)—O—Y, $(CH_2)_p$—C(O)—Y, $(CH_2)_p$—C(O)NR_3—Y, or $(CH_2)_p$—N(R_3)C(O)—Y; $R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 3-6.

In a further embodiment, $R_1$ can be $(CH_2)_p$—NR_3—Y.

In another embodiment, $R_2$ can be optionally substituted alkyl, containing 0, 1, 2, or 3 heteroatoms selected from O, S, or N; or optionally substituted arylalkyl.

In certain embodiments, $R_2$ can be a side chain of a naturally occurring amino acid.

In a further embodiment, $R_2$ can be $(CH_2)_p$—OR_4, $(CH_2)_p$—SR_4, $(CH_2)_p$—SOR_4, $(CH_2)_p$—SO_2R_4, $(CH_2)_p$—N(R_3)S(O)_2—R_4, $(CH_2)_p$—N(R_3)(SO_2)NR_3R_4, $(CH_2)_p$—NR_3R_4, $(CH_2)_p$—C(O)—O—R_4, $(CH_2)_p$—C(O)R_4, $(CH_2)_p$—C(O)NR_3R_4, or $(CH_2)_p$—N(R_3)C(O)R_4; $R_3$ and $R_4$ can be each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p can be 1-6

In a further embodiment, $R_2$ is $(CH_2)_p$—OR_4, $(CH_2)_p$—C(O)—O—R_4, $(CH_2)_p$—C(O)R_4, $(CH_2)_p$—C(O)NR_3R_4, or $(CH_2)_p$—N(R_3)C(O)R_4; $R_3$ and $R_4$ can be each independently selected at each occurrence from the following: H, optionally substituted alkyl, optionally substituted alkenyl or optionally substituted alkynyl, each containing 0, 1, 2, or 3 heteroatoms selected from 0, S, or N; optionally substituted aryl; optionally substituted heteroaryl; optionally substituted heterocyclic; or optionally substituted carbocyclic; and p can be 1-3.

In a further embodiment, $R_2$ can be $(CH_2)_p$—C(O)—O—R_4, where R4 is H and R' and R" are COOH, and R1 is $(CH2)_2$, and p can be 1-6.

In a further embodiment, the targeting moiety can be PBDA (4,4'-phosphinicobis(butane-1,3-dicarboxylic acid. PBDA can have a formula according to Formula 12.

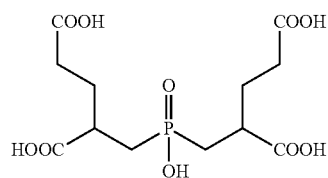

Formula 12

Methods of making PBDA based and urea based derivatives will be appreciated by those skilled in the art.

Photoacoustic Signaling Molecules

The targeted photoacoustic compounds described herein also include a photoacoustic signaling molecule. Suitable photoacoustic signaling molecules can absorb light from a light source (e.g. a laser) and emit ultrasonic waves that can be received by an ultrasound transducer. In some embodiments, the photoacoustic signaling molecules are tuned to absorb light in the tissue's "optical window" range of about 600-900 nm. Suitable photoacoustic signaling molecules can be dyes. Suitable dyes include, but are not limited to, Evans blue, indocyanine green, lymphazurin, methylene blue, ATTO-610, ATTO-620, ATTO-Rho 14, ATTO-633, ATTO, 647, ATTO-647N, ATTO-655, ATTO-Oxa12, ATTO-665, ATTO-680, ATTO-700, ATTO, 725, and ATTO-740. Dyes with suitable optical properties will be appreciated by those of skill in the art.

Linkers

The targeted photoacoustic compounds contain a linker, which couples the targeting moiety to the photoacoustic signaling molecule. The targeted photoacoustic compounds can include any suitable linker. Linkers can be used to form amid linkages, ester linkages, disulfide linkages, etc. Linkers can contain carbon atoms or heteroatoms. Linkers can be 1-50 atoms long. Linkers can be substituted with suitable substituents including but not limited to, hydrogen, alkyl, alkenyl, alkynl, amino, alkylamino, dialkylamino, trialkylamino, hydroxyl, alkoxy, halogen, aryl, heterocyclic, aromatic heterocyclic, cyano, amide carbamoyl, carboxylic acid, ester, thioetherm alkylthioetherm thiol, and ureido groups. It will be appreciated by those of skill in the art, that each of these groups can be in turn be substituted. The linker can be cleavable or non-cleavable. Cleavable linkers can be protease cleavable peptide linkers, nuclease sensitive nucleic acid linkers, lipase sensitive linkers, photo-cleavable linkers, heat-liable linkers, pH sensitive linkers, hypoxia sensitive linkers, photo-cleavable linkers, heat-liable linkers, enzyme cleavable linkers. Methods and techniques of making and testing linkers will be apparent to those of skill in the art.

Suitable linkers include, but are not limited to, 6-aminohexanoic acid, polyethylene glycol (PEG), polyethylene, polyalkyl, and polyether.

Methods and techniques of coupling the linker to the targeting moiety and signaling compound will be apparent to those of skill in the art.

Targeted Photoacoustic Compound Pharmaceutical Formulations

The targeted photoacoustic compounds described herein can be provided to a subject alone or as an ingredient, such as an active ingredient, in a pharmaceutical formulation. As such, also described herein are pharmaceutical formulations containing one or more of the targeted photoacoustic compounds described herein. In some embodiments, the pharmaceutical formulations contain an effective amount of targeted photoacoustic compounds described herein. The pharmaceutical formulations can be administered to a subject in need thereof. In some embodiments, the subject in need thereof can have a cancer. In other embodiments the subject in need thereof can have a PSMA positive cancer. In some embodiments, the cancer is prostate cancer. In other embodiments, the targeted photoacoustic compounds can be used in the manufacture of a medicament for the treatment of a cancer.

The pharmaceutical formulation can contain a homogenous population of targeted photoacoustic compounds. In these embodiments, all of the targeted photoacoustic compounds contained in the pharmaceutical formulation are the same. In other embodiments, the pharmaceutical formulation can contain a heterogeneous population of targeted photoacoustic compounds. In these embodiments, the population of targeted photoacoustic compounds contains at least two targeted photoacoustic compounds that are different from one another. The two different targeted photoacoustic compounds can vary from one another in the photoacoustic signaling molecule, the targeting moiety, and/or the linker contained therein.

Pharmaceutically Acceptable Carriers and Auxiliary Ingredients and Agents

The pharmaceutical formulations containing an effective amount of the targeted photoacoustic compounds described herein can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of the targeted photoacoustic compounds, the pharmaceutical formulation can also include an effective amount of auxiliary active agents, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Suitable compounds for the auxiliary active agents have been previously described herein in relation to the targeted photoacoustic compounds.

Effective Amounts of the Targeted Photoacoustic Compounds and Auxiliary Agents

The pharmaceutical formulations can contain an effective amount of the targeted photoacoustic compounds and/or an effective amount of an auxiliary agent. In some embodiments, the effective amount ranges from about 0.001 pg of the targeted photoacoustic compounds to about 1,000 μg of targeted photoacoustic compounds. In other embodiments, the concentration of the targeted photoacoustic compounds effective amount ranges from about 1 nM to about 50 nM.

In embodiments where there is an auxiliary active agent contained in the pharmaceutical formulation in addition to the targeted photoacoustic compounds, the effective amount of the auxiliary active agent will vary depending on the auxiliary active agent. In some embodiments, the effective amount of the auxiliary active agent ranges from 0.001 micrograms to about 1 milligrams. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

The auxiliary active agent can be included in the pharmaceutical formulation or can exist as a stand-alone compound or pharmaceutical formulation that is administered contemporaneously or sequentially with the conjugate compound, derivative thereof or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent ranges from 0.001 micrograms to about 1000 grams. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total auxiliary active agent pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total auxiliary agent pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, and intradermal. Such formulations may be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, this is a subject having cancer. In some embodiments, the cancer is prostate cancer.

Where appropriate, the dosage forms described herein can be microencapsulated. The dosage form can also be prepared to prolong or sustain the release of any ingredient. In some embodiments, the targeted photoacoustic compound is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the targeted photoacoustic compound, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the targeted photoacoustic compounds, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of a targeted photoacoustic compounds, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a conjugate compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once, once daily, or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulations. In addition to the targeted photoacoustic compound, auxiliary active ingredient, and/or pharmaceutically acceptable salt thereof, such a dosage form can contain a powder base such as lactose, glucose, trehalose, mannitol, and/or starch. In some of these embodiments, the conjugate compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for injection (i.v., s.q., i.c.v., i.m. etc.), can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

For some embodiments, the dosage form contains a predetermined amount of a conjugate compound per unit dose. In an embodiment, the predetermined amount of the conjugate compound is an effective amount of the targeted photoacoustic compounds to diagnose, treat, prevent, or mitigate the symptoms of cancer. In other embodiments, the predetermined amount of the targeted photoacoustic compounds is an appropriate fraction of the effective amount of the active ingredient. Such unit doses may therefore be administered once or more than once a day. Such pharmaceutical formulations may be prepared by any of the methods well known in the art.

Methods of Using the Targeted Photoacoustic Compounds and Formulations Thereof

The targeted photoacoustic compounds and pharmaceutical formulations thereof described herein can be used for the diagnosis, treatment, or prevention of a disease, disorder, syndrome, or a symptom thereof. In some embodiments, the targeted photoacoustic compounds or pharmaceutical formulations thereof can be used to diagnose, treat, or prevent a cancer or symptom thereof. The cancer can be a PSMA positive cancer or prostate cancer. The targeted photoacoustic compounds and pharmaceutical formulations thereof can be used as a contrast agent for optical and photoacoustic procedures.

An amount of the targeted photoacoustic compounds and pharmaceutical formulations thereof described herein can be administered to a subject in need thereof one or more times per day, week, month, or year. In some embodiments, the subject has one or more symptoms of a disease, condition, or syndrome. In some of these embodiments, the disease, condition, or syndrome can be cancer. In some embodiments, the cancer can be a PSMA positive cancer. In some embodiments, the cancer is prostate cancer. In some embodiments, the amount administered can be the effective amount of the targeted photoacoustic compounds or pharmaceutical formulations thereof. For example, the targeted photoacoustic compounds or pharmaceutical formulations thereof, can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the targeted photoacoustic compounds or pharmaceutical formulations thereof are administered one or more times per month, such as 1 to 5 times per month. In still further embodiments, the targeted photoacoustic compounds or pharmaceutical formulations thereof are administered one or more times per year, such as 1 to 11 times per year.

In embodiments where more than one of the targeted photoacoustic compounds, pharmaceutical formulations thereof, and/or auxiliary agent(s) are administered sequentially; the sequential administration may be close in time or remote in time. For example, administration of the second targeted photoacoustic compounds, pharmaceutical formulations thereof, and/or auxiliary agent(s) can occur within seconds or minutes (up to about 1 hour) after administration of the first agent (close in time). In other embodiments, administration of the second targeted photoacoustic compounds, pharmaceutical formulations thereof, and/or auxiliary agent(s) occurs at some other time that is more than an hour after administration of the first the targeted photoacoustic compounds or pharmaceutical formulations thereof.

The amount of the targeted photoacoustic compounds, pharmaceutical formulations thereof, and/or auxiliary agent(s) described herein can be administered in an amount ranging from about 0.01 mg to about 1 mg per day, as calculated as the free or unsalted pharmaceutical formulations. The amount of targeted photoacoustic compounds, pharmaceutical formulations thereof, and/or auxiliary agent(s) described herein can be administered in an amount ranging from about 0.01 µM to about 10 µM per day.

The targeted photoacoustic compounds or pharmaceutical formulations thereof described herein can be administered in combination with one or more other auxiliary agents that are independent of the pharmaceutical formulation. Suitable auxiliary agents include, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Suitable compounds for the auxiliary active agents have been previously described in relation to the targeted photoacoustic compounds. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

Kits

The targeted photoacoustic compounds or pharmaceutical formulations thereof described herein can be presented as a combination kit. As used herein, the terms "combination kit" or "kit of parts" refers to the targeted photoacoustic compounds or pharmaceutical formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the targeted photoacoustic compounds, pharmaceutical formulations thereof, or other auxiliary agent described herein are not administered simultaneously, the combination kit can contain each agent, compound, or formulation in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the targeted photoacoustic compounds, pharmaceutical formulations thereof, and/or other auxiliary agent contained therein, safety information regarding the content of the targeted photoacoustic compounds, pharmaceutical formulations thereof, and/or other auxiliary agent contained therein, information regarding the dosages, indications for use, and/or recommended treatment regimen(s) for the targeted photoacoustic compounds, pharmaceutical formulations thereof, and/or other auxiliary agent contained therein. In some embodiments, the instructions provide directions for administering the compounds, pharmaceutical formulations, or salts thereof to a subject having a cancer. In some embodiments, the cancer is a PSMA positive cancer. In some embodiments, the cancer is a prostate cancer.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1 Specificity of a PSMA Targeting Photoacoustic Compound

Clinical diagnosis of prostate cancer is made upon histological examination of the tissue obtained by biopsy, indicated for patients with abnormal prostate specific antigen (PSA) levels or rectal examination. The biopsy is not lesion directed as the imaging technique currently used to guide the procedure, transrectal ultrasound (TRUS), lacks the specificity to identify the malignancies and is used only to provide anatomical references within prostate. Although imaging plays an important role in all aspects of prostate cancer patient management, from diagnosis to treatment, currently no modality serves as a diagnostic tool. A PSMA targeting photoacoustic compound was created (FIG. 1). The PSMA targeting photoacoustic compound contains a urea-based PSMA targeting moiety coupled to a ATTO-740 dye via a 6-aminohexanoic acid molecule. The ATT-740 is a light absorbing dye.

Figure 2A:
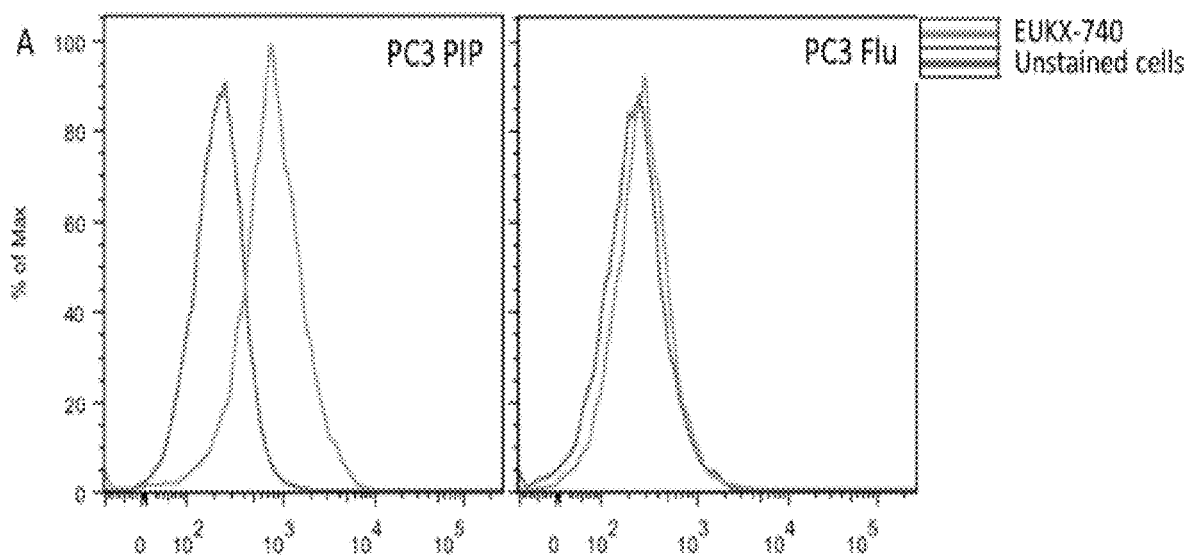
FIGS. 2A-2C demonstrate binding properties of a PSMA targeting photoacoustic compound to PSMA expressing cells.
Figure 2B:
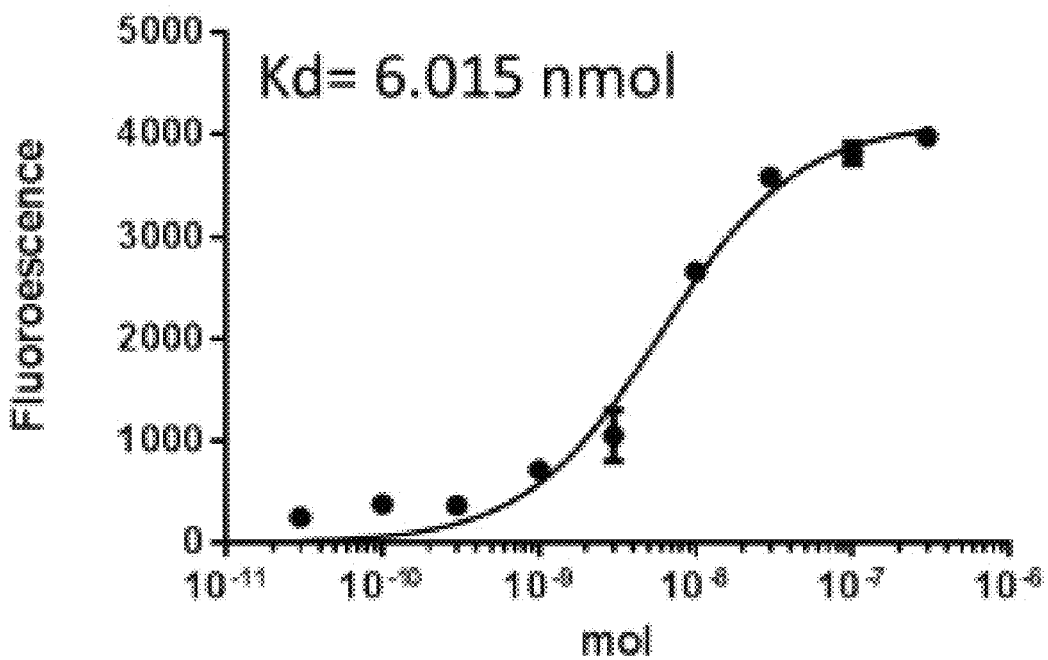
Figure 2C:
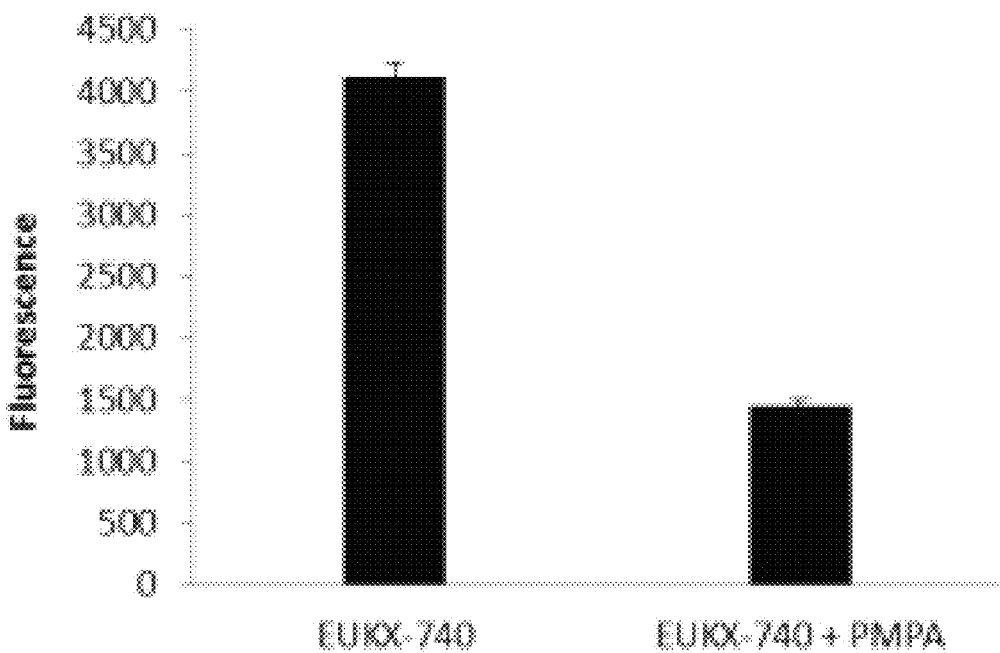

Binding of the PSMA targeting photoacoustic compound was evaluated in PC3 PIP cells, which express PSMA, and in PC3 Flu cells, which do not express PSMA. As is demonstrated in FIG. 2A, the targeting photoacoustic compound demonstrated high binding to PSMA expressing PC3 PiP cells and minimal binding to PC3 Flu cells. As demonstrated in FIG. 2B, the PSMA targeting photoacoustic compound has a strong affinity for PC3 PIP cells as evidenced by the low nanomolar dissociation constant (Kd=6.015 nM). As demonstrated in FIG. 2C, the binding of the PSMA targeting photoacoustic compound (0.1 nmol) to PC3 PIP cells was efficiently blocked by co-incubation with 0.5 nmol of a known PSMA inhibitor, 2-PMPA.

Example 2 The PSMA Targeting Photoacoustic Compound Binds the Surface of Cells

Figure 3:
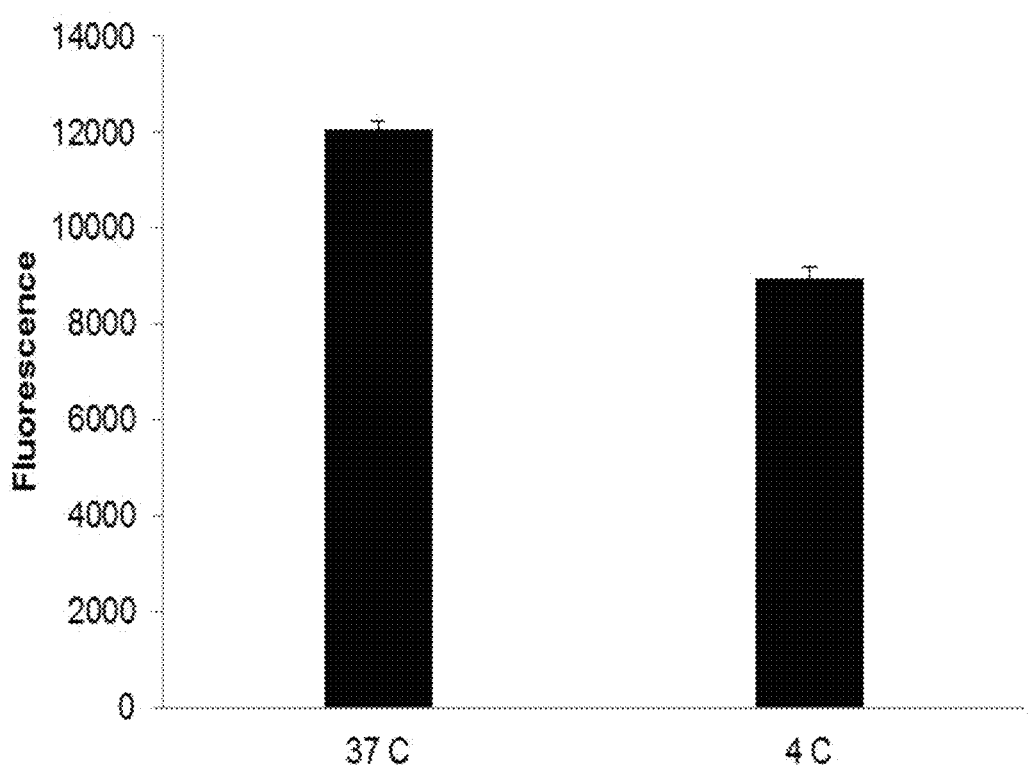
FIG. 3 demonstrates the specific binding of a PSMA targeting photoacoustic compound to the surface of PSMA expressing cells.

PSMA is a membrane bound receptor. To determine if the PSMA targeting photoacoustic compound was being actively transported through the cell membrane, PC3 PIP cells were incubated with 1 nmol of the PSMA targeting photoacoustic compound for 30 minutes at 37° C. or 4° C. As demonstrated in FIG. 3, after 30 minutes of exposure to the PC3 PIP cells the PSMA targeting photoacoustic compound was found mostly bound on the surface of the cells. Only about 25% of the PSMA targeting photoacoustic compound was internalized by passive diffusion.

Example 3 Binding of the PSMA Targeting Photoacoustic Compound in Prostate Tissue As normal prostate epithelium expresses PSMA, the PSMA targeting photoacoustic compound was tested in a model that accurately depicts normal prostate and primary prostate adenocarcinoma. The PSMA targeting photoacoustic compound was tested in tissue slice cultures (TSC). TSC are thin slices of human prostate tissue that maintain cellular heterogeneity and thus allow interrogation of binding to cancer and normal prostate epithelium often within the same tissue core. TSCs from freshly excised human prostate tissue from a single patient were incubated with 1.5 nmol of the agent for 30 minutes and imaged photoacoustically using 750 nm excitation wavelengths.

Figures 4A, 4B, 4C, 4D, 4E, 4F, 4G, 4H:
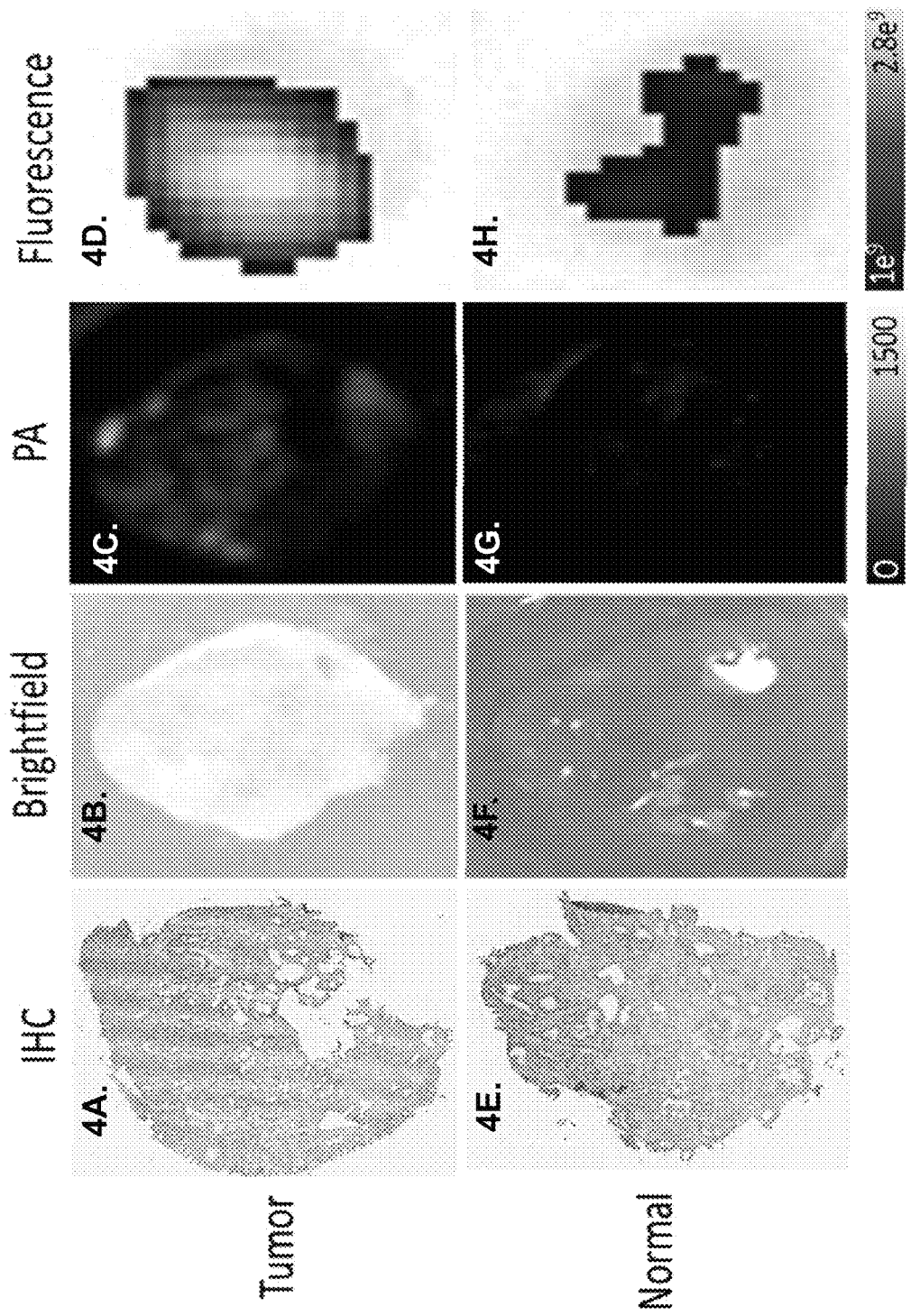
FIGS. 4A-4H demonstrate the differential binding of a PSMA targeting photoacoustic compound to normal prostate cells and cancerous prostate cells in prostate tissue.

Normal tissue or cancer was grossly identified in the fresh radical prostatectomy specimen and a core of tissue (about 8-mm in diameter) was aseptically bored and precision-cut at 300-μm (brightfield, FIGS. 4B and 4F)). After about one hour of recovery from slicing, tissue slices were incubated with 1.5 nmol a PSMA targeting photoacoustic compound, washed three times with PBS and immediately imaged both optically and photoacoustically (FIGS. 4C and 4G). Both fluorescent (FIGS. 4D and 4H) and photoacoustic (FIGS. 4C and 4G) images revealed clear distinction between normal and tumor tissue. The presence and Gleason grade of cancer as well as normal tissue was validated by H&E staining.

As demonstrated in FIGS. 4A-H, the PSMA targeting photoacoustic compound could differentiate between normal and prostate tumor tissue. This was also confirmed by fluorescence imaging (FIGS. 4D and 4H). Additionally, the PSMA targeting photoacoustic compound allowed visualization of the areas of high and low signal reflecting heterogeneity of the tissue and intermingling of cancer with benign areas. This was further confirmed by immunohistochemistry (FIGS. 4A and 4E).

The use of targeted photoacoustic agent for prostate cancer diagnosis has been evaluated in living subjects (mice) using an agent targeted against gastrin-releasing peptide receptor. The method showed promise as a noninvasive imaging modality that adds valuable molecular information to provide a potentially more specific prostate cancer diagnosis. See Levi et al. 2014. Clin. Cancer Res. 20:3721-3729, which is incorporated by reference as if expressed in its entirety. PSMA targeting photoacoustic compounds have not yet been evaluated in mice. The tissue culture model (TSC) described above offers a more accurate description of a human prostate cancer than subcutaneous tumor implants in mice and thus was chosen as a preferred model to evaluate PSMA targeted agents.

We claim:

1. A method of imaging a target cell in a subject in need thereof, comprising:
   administering a photoacoustic compound to the subject in need thereof;
   applying a light to the area of the subject to be imaged; and
   detecting ultrasonic waves emitted from the photoacoustic compound,
     wherein the photoacoustic compound consists of a targeting moiety and a photoacoustic signaling molecule, wherein the photoacoustic signaling molecule is coupled to the targeting moiety via a linker, and wherein the photoacoustic signaling molecule is selected from the group consisting of: Evans blue, lymphazurin, methylene blue, ATTO-610, ATTO-620, ATTO-Rho 14, ATTO-633, ATTO-647, ATTO-647N, ATTO-655, ATTO-Oxa12, ATTO-665, ATTO-680, ATTO-700, ATTO, 725, and ATTO-740, and wherein the targeting moiety has a Formula according to any one of Formulas 2-9, and 12:

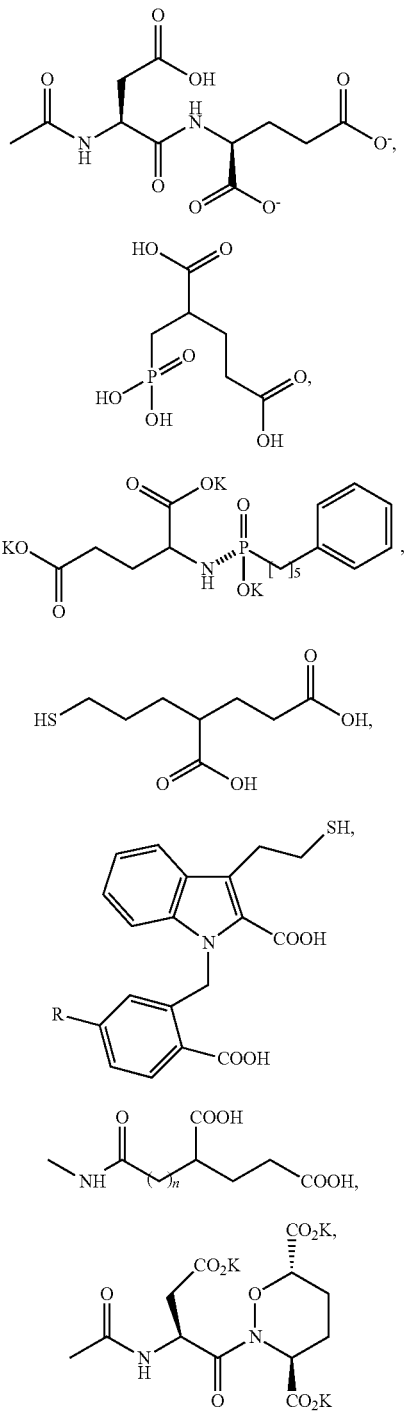

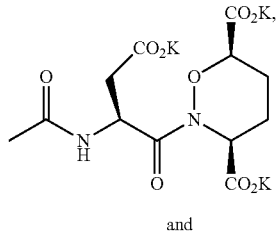

Formula 9 and

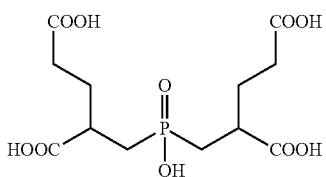

Formula 12 wherein, in Formula 6, R is H or —O-Me, and in Formula 7, n is between 1 and 50.

2. The method of claim 1, further comprising the step of converting the ultrasonic waves detected into a visual image.

3. The method of claim 1, wherein the ultrasonic waves are detected with an ultrasound transducer.

4. A compound consisting of a targeting moiety and a photoacoustic signaling molecule, wherein the photoacoustic signaling molecule is coupled to the targeting moiety via a linker, and wherein the photoacoustic signaling molecule is selected from the group consisting of: Evans blue, lymphazurin, methylene blue, ATTO-610, ATTO-620, ATTO-Rho 14, ATTO-633, ATTO-647, ATTO-647N, ATTO-655, ATTO-Oxa12, ATTO-665, ATTO-680, ATTO-700, ATTO, 725, and ATTO-740, and wherein the targeting moiety has a Formula according to any one of Formulas 2-9, and 12:

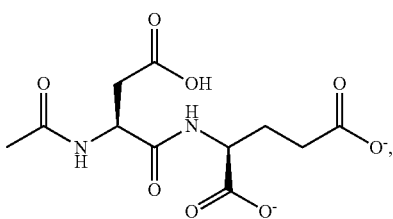

Formula 2

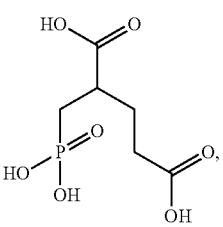

Formula 3

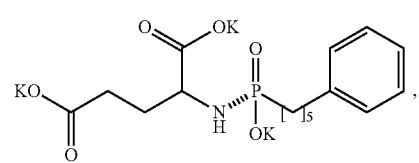

Formula 4

-continued

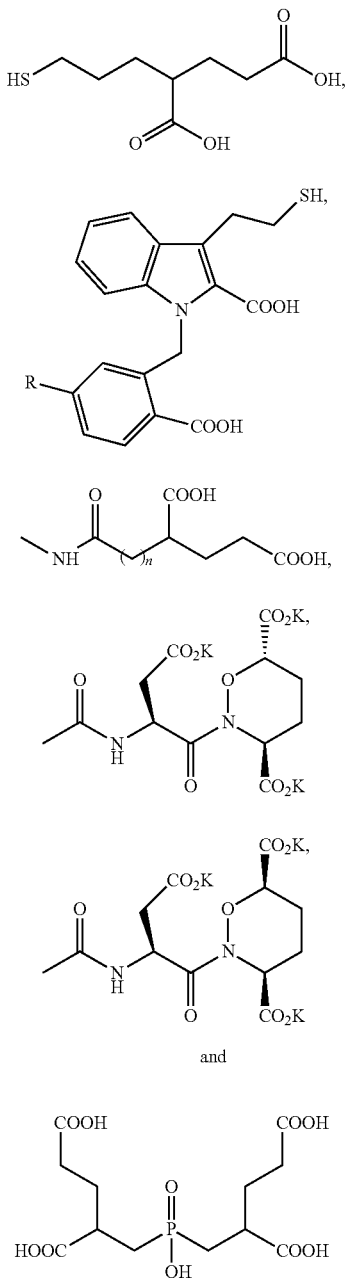

wherein, in Formula 6, R is H or —O-Me, and in Formula 7, n is between 1 and 50.

5. A pharmaceutical formulation comprising a photoacoustic compound consisting of a targeting moiety and a photoacoustic signaling molecule, wherein the photoacoustic signaling molecule is coupled to the targeting moiety via a linker, and wherein the photoacoustic signaling molecule is selected from the group consisting of: Evans blue, lymphazurin, methylene blue, ATTO-610, ATTO-620, ATTO-Rho 14, ATTO-633, ATTO-647, ATTO-647N, ATTO-655, ATTO-Oxa12, ATTO-665, ATTO-680, ATTO-700, ATTO, 725, and ATTO-740, and wherein the targeting moiety has a Formula according to any one of Formulas 2-9, and 12:

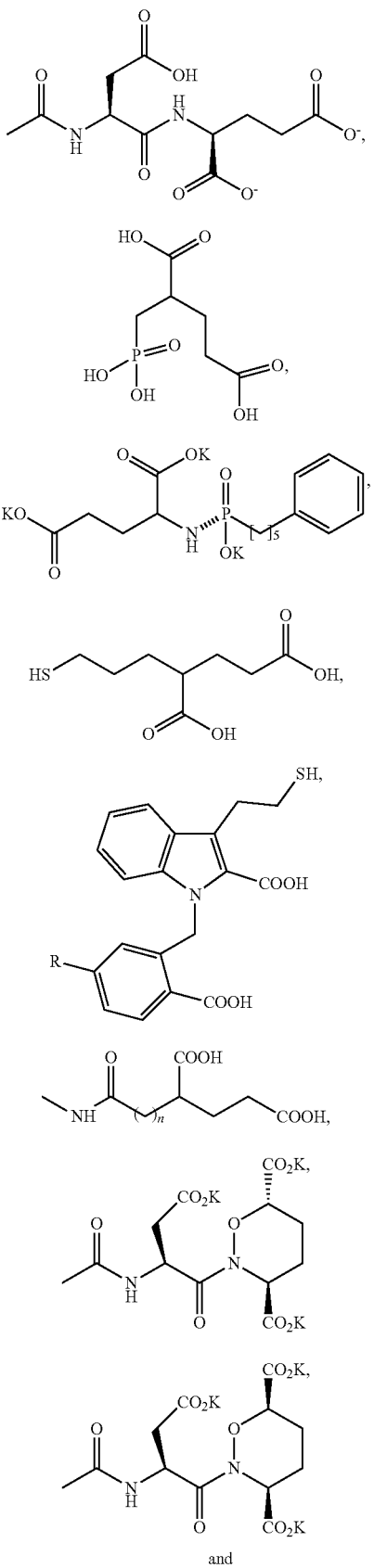

Formula 12
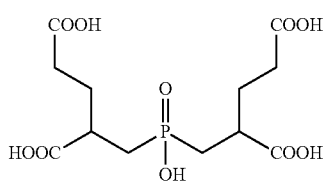
wherein, in Formula 6, R is H or —O-Me, in Formula 7, n is between 1 and 50; and
a pharmaceutically acceptable carrier.
6. The compound of claim 4, wherein the linker is 6-aminohexanoic acid.
7. The compound of claim 4, wherein the photoacoustic signaling molecule has a formula selected from the group consisting of:
ATTO-610
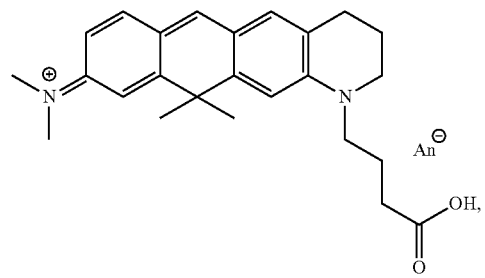
Atto-620
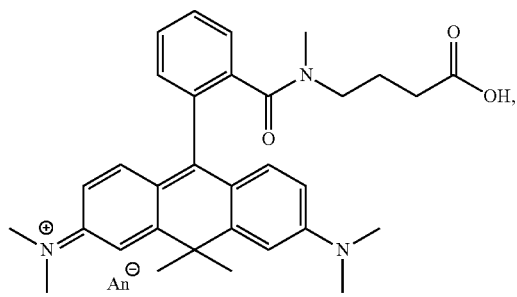
ATTO-Rho 14
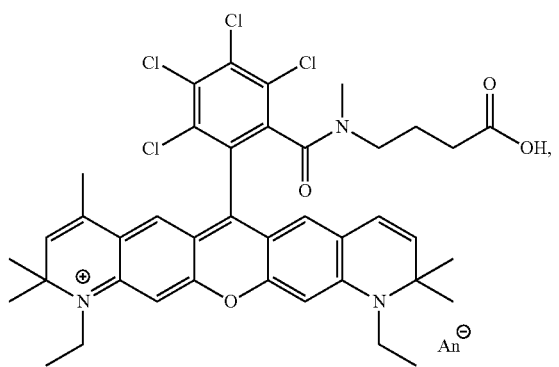
Atto-633
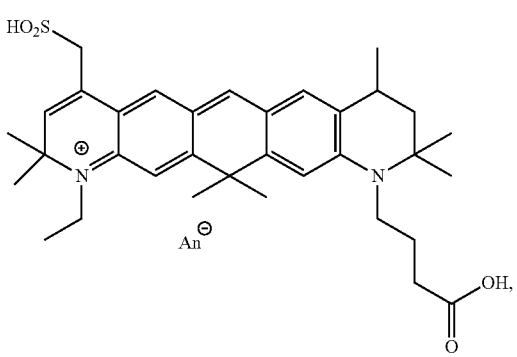
ATTO-647
ATTO-647N
ATTO-655
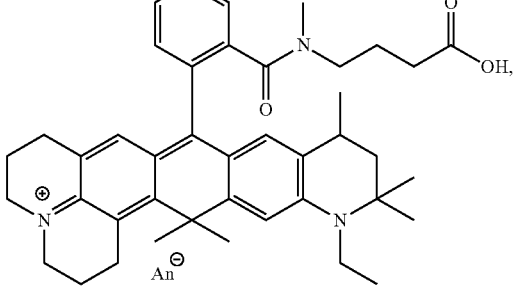
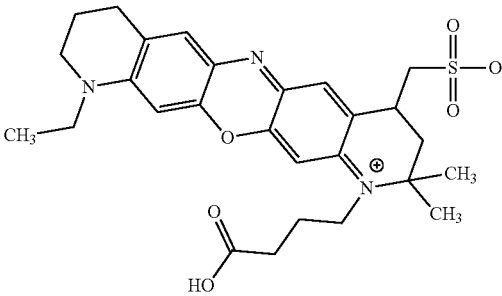

Atto-680
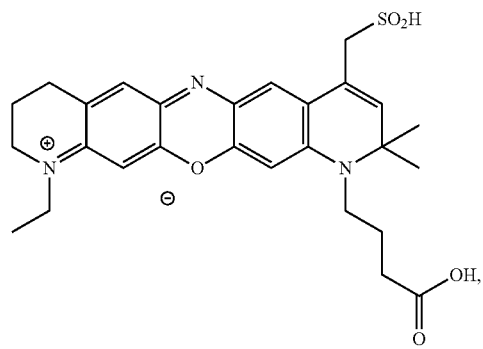
ATTO-700
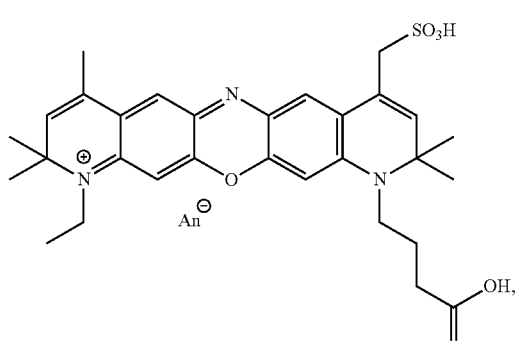
8. The pharmaceutical formulation of claim 5, wherein the linker is 6-aminohexanoic acid.
9. The pharmaceutical formulation of claim 5, wherein the photoacoustic signaling molecule has a formula selected from the group consisting of:
ATTO-610
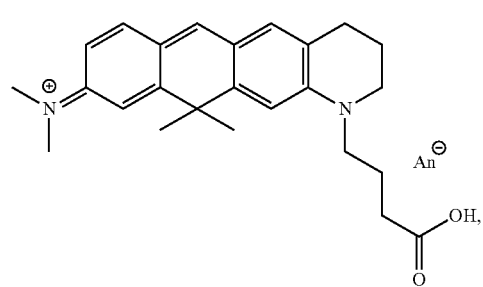
Atto-620
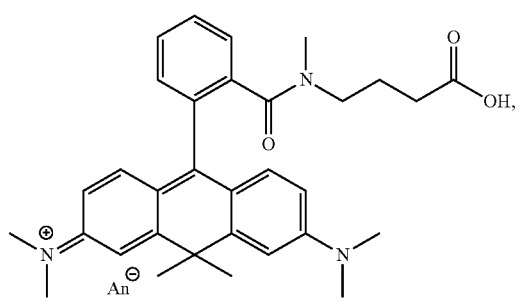
ATTO-Rho 14
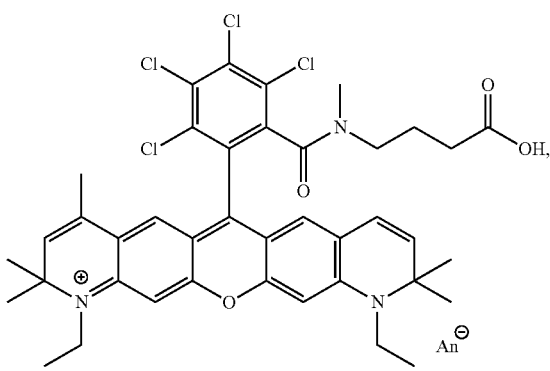
Atto-633
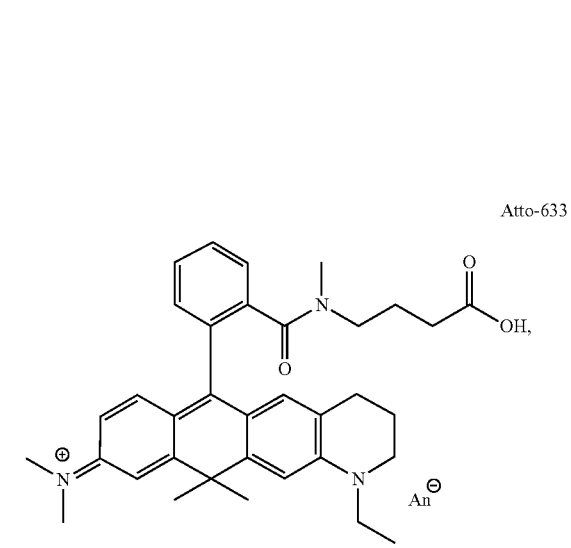
ATTO-647
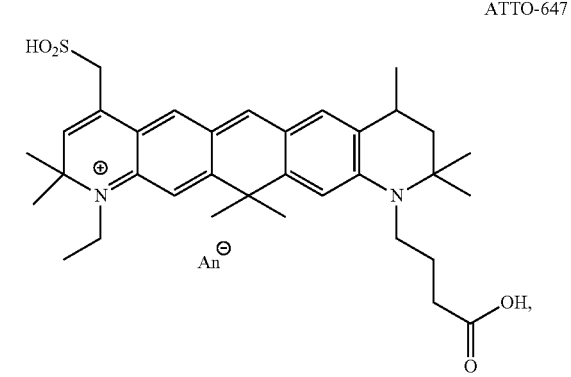

Atto-647N
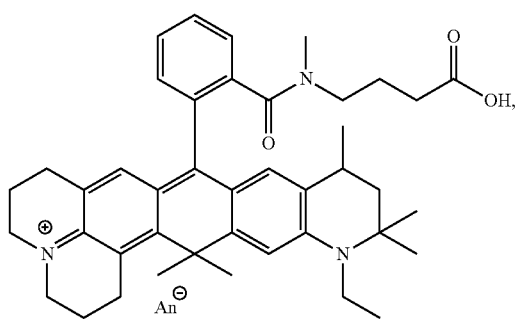
ATTO-655
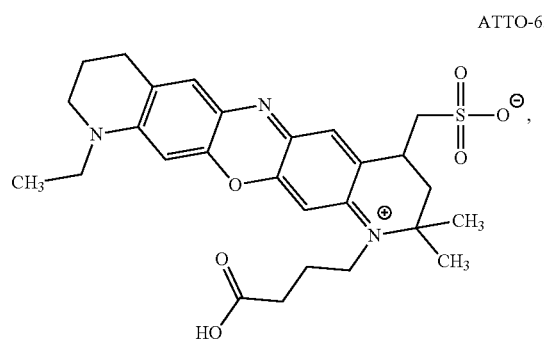
Atto-680
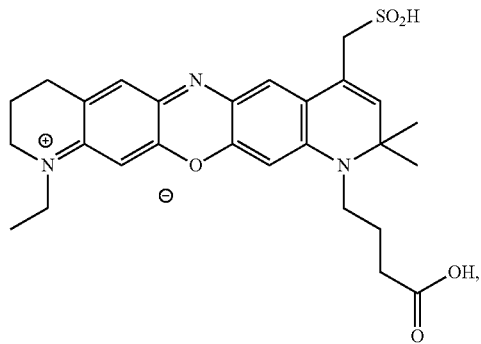
ATTO-700
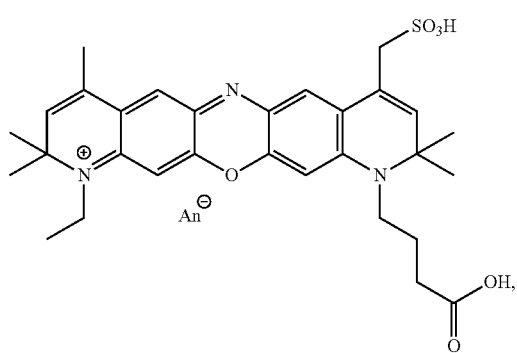
* * * * *